(12) United States Patent
Augello et al.

(10) Patent No.: US 6,602,718 B1
(45) Date of Patent: Aug. 5, 2003

(54) METHOD AND DEVICE FOR COLLECTING AND STABILIZING A BIOLOGICAL SAMPLE

(75) Inventors: Frank A. Augello, Cedar Knolls, NJ (US); Lynne Rainen, Maplewood, NJ (US); Matthew Walenciak, Madison, NJ (US); Uwe Oelmüller, Erkrath (DE); Ralf Wyrich, Grevenbroich (DE); Helge Bastian, Mettmann (DE)

(73) Assignees: Becton, Dickinson and Company, Franklin Lakes, NJ (US); Qiagen GmbH, Hilden (DE)

( * ) Notice: Subject to any disclaimer, the term of this patent is extended or adjusted under 35 U.S.C. 154(b) by 0 days.

(21) Appl. No.: 09/707,745

(22) Filed: Nov. 8, 2000

(51) Int. Cl.[7] ............................. G01N 1/00; C12M 1/24; C12M 1/34

(52) U.S. Cl. ............................. 436/176; 436/8; 436/18; 435/2; 435/6; 435/260; 435/287.2; 422/99; 422/102; 252/408.1

(58) Field of Search ............................. 436/8, 18, 174, 436/176; 435/2, 4, 6, 269, 270, 287.2; 422/99, 102, 913, 939, 940, 944; 252/408.1

(56) References Cited

U.S. PATENT DOCUMENTS

| | | | |
|---|---|---|---|
| 3,847,738 A | * 11/1974 | Brake et al. | 435/2 |
| 4,040,785 A | * 8/1977 | Kim et al. | 435/2 |
| 4,812,310 A | * 3/1989 | Sato et al. | 424/529 |
| 5,010,183 A | 4/1991 | Macfarlane | 536/27 |
| 5,300,635 A | * 4/1994 | Macfarlane | 536/25.4 |
| 5,346,994 A | 9/1994 | Chomczynski | |
| 5,459,253 A | * 10/1995 | Wolin et al. | 435/6 |
| 5,610,287 A | 3/1997 | Nikiforov et al. | 536/24.3 |
| 5,620,852 A | 4/1997 | Lin et al. | |
| 5,637,687 A | 6/1997 | Wiggins | |
| 5,654,179 A | 8/1997 | Lin | |
| 5,667,963 A | 9/1997 | Smith et al. | 435/2 |
| 5,728,822 A | 3/1998 | Macfarlane | 536/25.41 |
| 5,744,520 A | * 4/1998 | Kmiecik-Lawrynowicz et al. | 523/205 |

(List continued on next page.)

FOREIGN PATENT DOCUMENTS

| | | |
|---|---|---|
| DE | 100 31 236 A1 | 1/2002 |
| EP | 0818542 | 1/1998 |
| WO | WO 94/18156 | 8/1994 |
| WO | 0009746 | 2/2000 |
| WO | WO 02/00599 A1 | 1/2002 |
| WO | WO 02/00600 A1 | 1/2002 |

OTHER PUBLICATIONS

Oelrichs Robert B et al; "The Explosive Human Immunodeficiency Virus Type 1 Epidemic among Injecting Drug Users of Kathmandu, Nepal, is Caused by a Subtype C Virus of Restricted Genetic Diversity", Journal of Virology, vol. 74, No. 3, Feb. 2000, pp. 1149–1157.

Schmidt Warren N et al; "Direct Detection of Hepatitis C Virus (HCV) RNA From Whole Blood, and Comparison with HCV RNA in Plasma and Peripheral Blood Mononuclear Cells", Journal of Medical Virology, vol. 47, No. 2, 1995, pp. 153–160.

Primary Examiner—Maureen M. Wallenhorst
(74) Attorney, Agent, or Firm—Roylance, Abrams, Berdo & Goodman, L.L.P.

(57) ABSTRACT

A collection container and method for collecting a predetermined volume of a biological sample, and particularly a whole blood sample, includes an effective amount of at least one stabilizing agent. The stabilizing agent is able to stabilize nucleic acids in the biological sample at the point of collection to prevent enzymatic degradation of the nucleic acids. The stabilizing agents include cationic compounds, detergents, particularly cationic detergents, chaotropic salts, ribonuclease inhibitors, chelating agents, and mixtures thereof.

51 Claims, 1 Drawing Sheet

U.S. PATENT DOCUMENTS

| | | |
|---|---|---|
| 5,747,663 A | 5/1998 | Colpan et al. ............ 536/25.4 |
| 5,777,099 A | 7/1998 | Mehra |
| 5,792,651 A | 8/1998 | Colpan et al. ............ 435/270 |
| 5,860,937 A * | 1/1999 | Cohen ................... 210/359 |
| 5,906,744 A * | 5/1999 | Carroll et al. ............ 210/516 |
| 5,939,259 A | 8/1999 | Harvey et al. ............ 435/6 |
| 5,985,572 A | 11/1999 | Macfarlane ............... 435/6 |
| 5,990,301 A | 11/1999 | Colpan et al. ............ 536/25.4 |
| 6,020,186 A | 2/2000 | Henco et al. ............ 435/287.2 |
| 6,043,032 A | 3/2000 | Yamagishi |
| 6,114,108 A | 9/2000 | Budowsky ................ 435/2 |
| 6,168,922 B1 | 1/2001 | Harvey et al. ............ 435/6 |
| 6,218,531 B1 | 4/2001 | Ekenberg |
| 6,231,815 B1 | 5/2001 | Bainczyk et al. |
| 6,258,930 B1 * | 7/2001 | Gauch et al. ............ 241/180 |
| 6,274,386 B1 | 8/2001 | Harttig |
| 6,409,528 B1 * | 6/2002 | Bodnar .................. 422/102 |

* cited by examiner

Fig. 1

METHOD AND DEVICE FOR COLLECTING AND STABILIZING A BIOLOGICAL SAMPLE

FIELD OF THE INVENTION

The present invention is directed to a method and device for collecting a biological sample, and particularly a whole blood sample, directly from a patient. More particularly, the invention relates to evacuated fluid sample containers having a stabilizing additive contained therein for stabilizing nucleic acids immediately on collection of a biological sample.

BACKGROUND OF THE INVENTION

Sample collection containers have been in common use for many years for collecting and storing blood and other body fluids or samples. Typically, the collection containers are glass or plastic tubes having a resilient stopper. These glass or plastic tubes are often used for blood collection.

Blood collection tubes are available where the tube is evacuated to draw a volume of blood into the tube. The tubes can have various additives, such as ethylenediaminetetraacetic acid (EDTA) contained therein for preparing the blood sample for a particular test. A common additive is an anticoagulation agent. Typically, the anticoagulation additive is a buffered citrate or heparin in an aqueous solution. The aqueous citrate is combined with the blood sample in a specified amount to determine the amount of an anticoagulant needed for conducting certain tests. These devices can be used only for serological testing since the additives do not stabilize the nucleic acids in the sample. During shipment, labile RNA molecules are degraded enzymatically so that subsequent RNA separation and analysis is difficult. Furthermore, mechanical irritation or disruption of cells during blood collection and transport causes the induction of gene transcription with the concomitant over- or underproduction of certain mRNA species.

Common additives including anticoagulants to maintain the blood sample in an anticoagulated state are used for performing various processing steps. For example, anticoagulants are typically used in blood samples prior to centrifuging to separate the blood into cell layers. An example of this type of sample tube containing an anticoagulant is disclosed in U.S. Pat. No. 5,667,963 to Smith et al.

In recent years there has been an increase in interest in the field of biological, medical and pharmacological science in the study of gene activities and nucleic acids obtained from biological samples. In particular, ribonucleic acids can provide extensive information of the genetic origin and functional activity of the cell. This information may be used in clinical practice to diagnose infections, detect the presence of cells expressing oncogenes, detect heredity disorders, monitor the state of host defense mechanisms and to determine the HLA type or other marker of identity.

A number of methods exist for isolating RNA which entails disruption of the cell and liberating RNA into solution. Other methods exist for protecting RNA from enzymatic digestion by endogenous RNases. The RNA can then be separated from the DNA and protein, which is solubilized along with the RNA. These processes are usually performed in stepwise fashion rather than for simultaneously lysing cells, solubilizing RNA and inhibiting RNases. Some methods for lysing cells and inhibiting RNases are known that use chaotropic salts of guanidinium.

A commonly used process for isolating RNA involves homogenizing cells in guanidinium isothiocyanate, followed by the sequential addition of sodium acetates and phenol, and chloroform/isoamyl alcohol. After centrifugation, RNA is precipitated from the upper layer by the addition of alcohol. Other methods include the addition of hot phenol to a cell suspension, followed by alcohol precipitation.

Anionic and cationic surfactants are used to lyse cells and liberate cytoplasmic RNA. An example of a method for lysing cells and simultaneously precipitating RNA and DNA from solution is disclosed in U.S. Pat. No. 5,010,183 to Macfarlane. In this process, the RNA is made insoluble. A 2% solution of the surfactant benzyldimethyl n-hexadecylammonium chloride together with 40% urea and other additives are added to a cell suspension. The suspension is then centrifuged to recover a pellet of the insoluble materials. The pellet is resuspended in ethanol and the RNA and DNA are precipitated by the addition of a salt.

A method for analyzing RNA isolated from blood uses amplification methods including polymerase chain reaction to detect sequences of RNA in minute amounts. One difficulty in analyzing RNA is the separation of the RNA from the protein and the DNA in the cell before the RNA is degraded by nucleases. RNase and other nucleases are present in the blood in sufficient quantities to destroy unprotected RNA. Therefore, it is desirable to use a method of isolating RNA from cells in a manner to prevent hydrolysis of RNA by nucleases.

The blood collection methods currently in common use are able to collect and retain the blood for analysis at a later time. The collection device can include an anticoagulant to prevent coagulation during storage. However, the nucleases present in the blood hydrolyze some RNA species during storage and transport while mechanical irritation or disruption of cells during blood collection causes induction of some RNA species. These preanalytical sample handling factors result in under- or overrepresentation of mRNA species and eventual degradation of total RNA as determined by molecular diagnostic test methods. In addition, gene induction can result in increased levels of RNA in the sample, which can give false results. Accordingly, there is a continuing need in the industry for an improved method and collection device for blood and other biological samples that preserve the in vivo transcription profile for nucleic acid-based tests.

SUMMARY OF THE INVENTION

The present invention is directed to a method and device for collecting a biological sample. More particularly, the invention is directed to a collection container and to a method of collecting a biological sample with a stabilizing additive to stabilize the sample and preserve the in vivo transcription profile.

Accordingly, a primary aspect of the invention is to provide a method and device for collecting a biological sample, and particularly whole blood, directly from a patient in the presence of a stabilizer to stabilize and preserve RNA and prevent gene induction in the sample. The stabilizing additive is present in an effective amount to stabilize the nucleic acids, particularly RNA, and stop gene induction.

A further object of the invention is to provide a method and device for stabilizing nucleic acids in a biological sample and to lyse cells, bacteria, viruses and reticulocytes.

Another object of the invention is to provide a collection container for receiving and collecting a biological sample where the container is pre-filled with a measured quantity of a nucleic acid stabilizing agent.

A further object of the invention is to provide a method for stabilizing a biological sample, and particularly whole blood, immediately upon collection from the patient.

Still another object of the invention is to provide a method for preventing induced transcription of RNA in a biological sample immediately on collection of the biological sample.

Another object of the invention is to provide an evacuated container containing an effective amount of a nucleic acid stabilizing agent, where the container has an internal pressure to draw a predetermined volume of a biological sample into the container.

A further object of the invention is to provide a blood collection container for collecting an amount of blood and mixing the blood with a nucleic acid stabilizing agent at the point of collection to preserve the nucleic acids and prevent gene induction such that analysis can be conducted at a later time.

Another object of the invention is to provide a method of stabilizing blood by collecting the blood sample in a container having a nucleic acid stabilizing agent and a buffer. The nucleic acid stabilizing agent can be a detergent, a chaotropic salt, RNase inhibitors, chelating agents, or mixtures thereof. The pH of the resulting mixture is adjusted to stabilize the nucleic acids and promote efficient recovery of the analyte.

Still another object of the invention is to provide a method of stabilizing nucleic acids in a blood sample collection device at about pH 2 to about pH 5 in the presence of at least one stabilizing agent.

The objects of the invention are basically attained by providing an apparatus for collecting a biological sample. The apparatus includes a container comprising a side wall, a bottom wall, and an open end defining an internal chamber, and a closure closing the open end. The container includes at least one stabilizing component in an effective amount to stabilize and preserve the biological sample. The container can be pre-filled with the stabilizing agent.

The objects of the invention are further attained by providing a method of stabilizing a biological sample comprising the steps of: providing a sample collection container having a side wall, and a bottom defining an internal chamber. The container contains at least one stabilizing agent in an amount and concentration sufficient to stabilize and preserve a biological sample. A biological sample is obtained and immediately introduced into the container and the biological sample is mixed with the stabilizing agent to form a stabilized biological sample.

The objects of the invention are also attained by providing a method of collecting and stabilizing a whole blood or other biological sample. The method comprises providing a sample collection container having a side wall, a bottom wall and a closure member forming an internal chamber. The container encloses an effective amount of an aqueous solution or dispersion of a nucleic acid stabilizing agent to stabilize and preserve nucleic acids and/or the transcriptional profile in a whole blood sample. The internal chamber has pressure less than atmospheric pressure. A whole blood sample is collected directly from a patient in the collection container and the blood sample is mixed with the stabilizing agent to form a stable whole blood sample.

These objects, advantages and other salient features of the invention will become apparent from the annexed drawing and the following detailed description of the invention.

BRIEF DESCRIPTION OF THE DRAWING

The following is a brief description of the drawing, in which.

DETAILED DESCRIPTION OF THE INVENTION

The present invention is directed to a method and device for stabilizing and preserving a biological sample. More particularly, the invention is directed to a method and device for stabilizing nucleic acids and/or preventing gene induction in a biological sample. In preferred embodiments of the invention, the device is a pre-filled container containing an amount of a nucleic acid stabilizing agent.

The biological sample can be a body fluid withdrawn from a patient. In one embodiment, the biological fluid is whole blood. Examples of other biological samples include cell-containing compositions such as red blood cell concentrates, platelet concentrates, leukocyte concentrates, plasma, serum, urine, bone marrow aspirates, cerebral spinal fluid, tissue, cells, and other body fluids.

Figure 1:
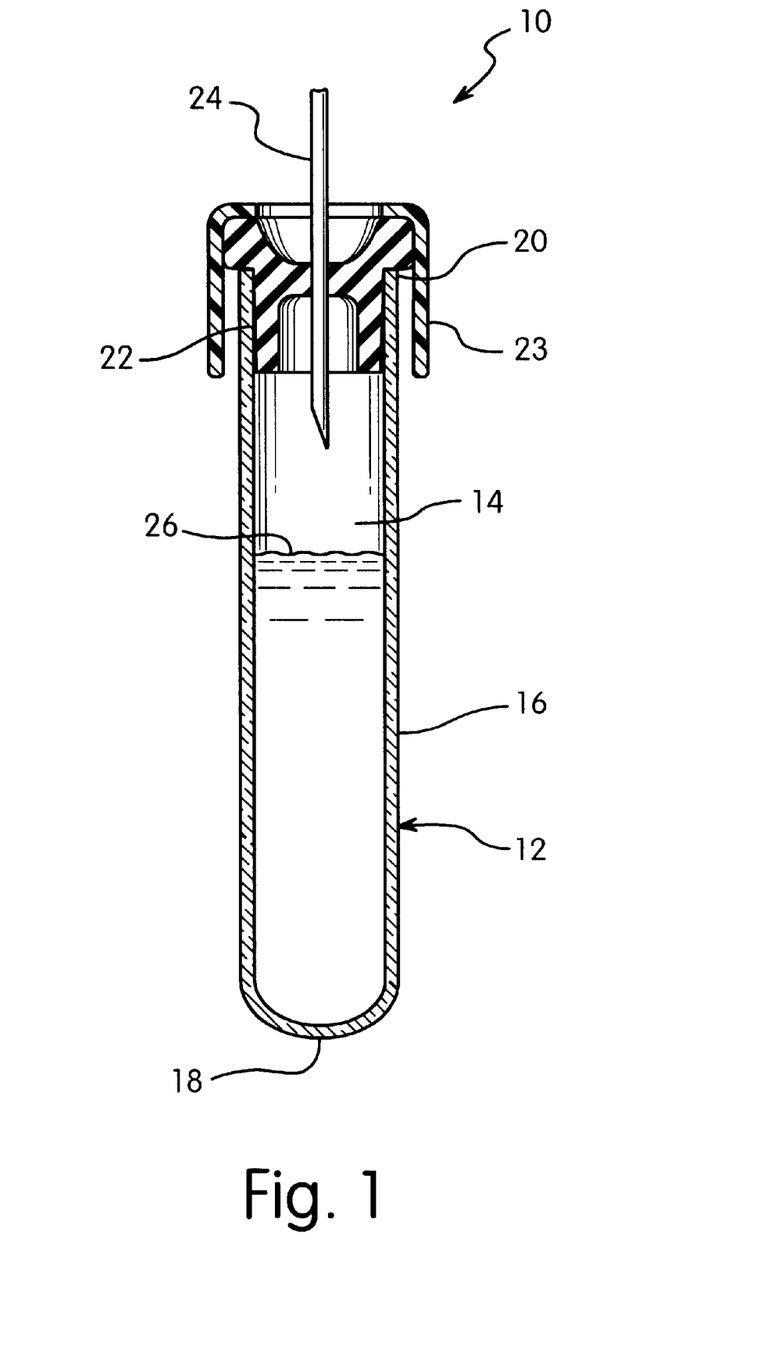
FIG. 1 is a cross-sectional side view of the container in one embodiment of the invention.

In a preferred embodiment, the device 10 is for drawing a blood sample directly from a patient for stabilizing the nucleic acids immediately at the point of collection. Referring to FIG. 1, device 10 includes a container 12 defining a chamber 14. In the embodiment illustrated, container 12 is a hollow tube having a side wall 16, a closed bottom end 18 and an open top end 20. Container 12 is dimensioned for collecting a suitable volume of a biological fluid. A resilient closure 22 is positioned in open top end 20 to close container 12. Preferably, closure 22 forms a seal capable of effectively closing container 12 and retaining a biological sample in chamber 14. A protective shield 23 overlies closure 22.

Container 12 can be made of glass, plastic or other suitable materials. Plastic materials can be oxygen impermeable materials or contain an oxygen impermeable layer. Alternatively, container 12 can be made of a water and air permeable plastic material. Preferably, chamber 14 maintains a pressure differential between atmospheric pressure and is at a pressure less than atmospheric pressure. The pressure in chamber 14 is selected to draw a predetermined volume of a biological sample into chamber 14. Typically, a biological sample is drawn into chamber 14 by piercing closure 22 with a needle 24 or cannula as known in the art. An example of a suitable container 12 and closure 22 are disclosed in U.S. Pat. No. 5,860,937 to Cohen, which is hereby incorporated by reference in its entirety.

Container 12 is preferably made of a transparent material. Examples of suitable transparent thermoplastic materials include polycarbonates, polyethylene, polypropylene, polyethylene-terephthalate. Container 12 has a suitable dimension selected according to the required volume of the biological sample being collected. In one embodiment, container 12 has a tubular shape with an axial length of about 100-mm and a diameter of about 13-mm to 16-mm.

Closure 22 is made of a resilient material capable of maintaining an internal pressure differential less than atmospheric and that can be pierced by a needle to introduce a biological sample into container 12. Suitable materials for closure include, for example, silicone rubber, natural rubber, styrene butadiene rubber, ethylene-propylene copolymers and polychloroprene. Container 12 also contains a stabilizing additive 26. The stabilizing additive 26 is preferably a liquid containing a stabilizing agent and is included in an effective amount to mix with the biological sample and stabilize the nucleic acids and/or prevent gene induction of the cells or nucleic acids contained therein. In one embodiment, the internal pressure of container 12 and the volume of stabilizing additive 26 are selected to provide the necessary concentration of the stabilizing agent for the volume of the biological sample collected. In one preferred embodiment, the internal pressure of container 12 is selected to draw a predetermined volume of about 2.5 ml of a biological sample into container 12 containing an effective volume of stabilizing additive 26 for stabilizing the volume of the biological sample. In alternative embodiments, container 12 can have an internal pressure at substantially atmospheric pressure.

In one embodiment, container 12 is made of a plastic that is water and gas permeable. Water loss by evaporation of the stabilizing agent through the permeable wall of the container increases the concentration of the stabilizing agent and decreases the pressure within the container. The diffusion of oxygen through the wall of the tube has the effect of decreasing the vacuum in the container. The water and oxygen permeability properties of the container are selected to maintain the desired pressure differential within the container for the desired shelf life of the container. The shelf life is optimized by balancing the oxygen permeability with the water loss. Preferably, the container has a shelf life of about one year.

Stabilizing additive 26 is typically an aqueous solution or dispersion of at least one active stabilizing agent that is included in the container as a pre-filled container. Stabilizing additive 26 preferably contains at least one stabilizing agent in a concentration capable of stabilizing nucleic acids in the biological sample, and particularly a whole blood sample. The stabilizing agents are preferably able to stabilize effectively DNA and RNA including mRNA, tRNA and cRNA. Examples of suitable stabilizing agents for stabilizing and preserving nucleic acids and/or preventing gene induction include cationic compounds, detergents, chaotropic salts, ribonuclease inhibitors, chelating agents, and mixtures thereof. A suitable ribonuclease inhibitor is placental RNAse inhibitor protein. Examples of chaotropic salts include urea, formaldehyde, guanidinium isothiocyanate, guanidinium hydrochloride, formamide, dimethylsulfoxide, ethylene glycol and tetrafluoroacetate.

The stabilizing agent can also include another component for treating the biological sample. For example, chemical agents can be included to permeabilize or lyse viruses and cells. Other components include proteinases, phenol, phenol/chloroform mixtures, alcohols, aldehydes, ketones and organic acids.

The detergents can be anionic detergents, cationic detergents or nonionic detergents. The anionic detergent can be, for example, sodium dodecyl sulfate. Nonionic detergents can be, for example, ethylene oxide condensation products, such as ethoxylated fatty acid esters of polyhydric alcohols. A preferred nonionic detergent is a polyoxyethylene sorbitan monolaurate sold under the trade name TWEEN 20 by Sigma Chemical Co. The detergents are included in an effective amount to lyse the cells and form micelles and other complexes with the nucleic acids.

In preferred embodiments, the stabilizing agent is a cationic compound having the general formula $YR_1R_2R_3R_4\ X$ wherein Y is nitrogen or phosphorous; $R_1$, $R_2$, $R_3$, and $R_4$ are independently branched or non-branched alkyl, $C_6$–$C_{20}$ aryl, or $C_6$–$C_{26}$ aralkyl, and X is an organic or inorganic anion.

The anion can be an anion of an inorganic acid such as the HX where X is fluorine, chlorine, bromine or iodine, with chlorine and bromine being preferred. The anion can also be the anion of a mono-, di- or tricarboxylic acid. Typically, the anion of the cationic compound is selected from the group consisting of phosphate, oxalate, malonate, succinate, citrate, bromide and chloride.

When $R_1$, $R_2$, $R_3$, and $R_4$ are aryl groups, the aryl groups independently can be, for example, phenyl, lower alkyl-substituted benzyl, and/or halogenated benzyl. In one embodiment $R_1$ is a $C_{12}$, $C_{14}$, or $C_{16}$ alkyl and $R_2$, $R_3$, and $R_4$ are methyl groups. In a preferred embodiment, Y is nitrogen and the stabilizing agent is a quaternary amine. Suitable quaternary amines include alkyltrimethylammonium where the alkyl group has 12, 14 or 16 carbons. One preferred cationic compound is tetradecyltrimethyl ammonium oxalate. Other suitable quaternary amines include alkyltrimethylammonium where the alkyl group includes 12, 14, 16 or 18 carbons. Examples of suitable quaternary amine surfactants are disclosed in U.S. Pat. No. 5,728,822 to Macfarlane, which is hereby incorporated by reference in its entirety.

In preferred embodiments of the invention the stabilizing agent is a cationic compound and includes a proton donor. It has been found that the addition of a proton donor to the cationic compounds increases the ability of the cationic compounds to stabilize the nucleic acids in the biological sample. Examples of suitable proton donors include monocarboxylic acids, alkenyl carboxylic acids, $C_2$–$C_6$ aliphatic mono- and dicarboxylic acids, aliphatic ketodicarboxylic acids, amino acids, mineral acids and mixtures thereof. Examples of suitable aliphatic carboxylic acids include $C_1$–$C_6$ alkyl carboxylic acids, such as acetic acid, propionic acid, n-butanoic acid, n-pentanoic acid, isopentanoic acid, 2-methylbutanoic acid, 2,2 dimethylpropionic acid, n-hexanoic acid, n-octanoic acid, n-decanoic acid, and dodecanoic acid. Examples of alkenyl carboxylic acids include acrylic acid, methacrylic acid, butenoic acid, isobutenoic acid and mixtures thereof.

The dicarboxylic acids of the proton donor are selected from the consisting of oxalic acid, malonic acid, succinic acid, glutaric acid, adipic acid and mixtures thereof. Examples of hydroxyl-containing acids include tartaric acid and malic acid. Suitable amino acids are selected from the group consisting of glycine, alanine, valine, leucine, isoleucine and mixtures thereof.

The quantity of stabilizing additive 26 in container 12 is determined by the internal volume of container 12, the internal pressure and the volume of the biological sample drawn into the container. In the illustrated embodiment, container 12 has an axial length of about 100-mm and a diameter of about 16-mm and has an internal pressure to draw a biological sample of about 2.5-ml.

Stabilizing additive 26 typically contains about 50 mg to about 90 mg per ml of the carrier liquid. Preferably, stabilizing additive 26 is an aqueous medium containing about 60 mg/ml to about 80 mg/ml, and most preferably about 70 mg/ml. The volume of stabilizing additive 26 in container 12 is about 6 to 8 ml, and preferably about 7 ml.

In one preferred embodiment, stabilizing additive 26 includes about 70 mg/ml of a nucleic acid stabilizing agent and is mixed with whole blood drawn directly from a patient. The blood is mixed with the liquid in a ratio of about 1:2 to about 1:3.5, preferably about 1:2.5 to about 1:1.3, and most preferably about 1:2.7 to about 1:2.8 by volume.

The concentration of the stabilizing agent is sufficient to stabilize the nucleic acids. In one preferred embodiment, the biological sample is whole blood. The concentration of the stabilizing agent in an amount of about 8 to about 12 mg/ml of blood, preferably about 9 to about 11 mg/ml, and more preferably about 10 mg/ml of blood.

The method of the invention is performed by obtaining a biological sample and introducing the sample into the container containing the stabilizing additive. In preferred embodiments the biological sample is prepared and immediately introduced directly into the collection container. In certain embodiments, the biological sample is introduced directly into the collection container with out any intervening process steps. It has been found that collecting the biological sample directly from the patient, such as when collecting a whole blood sample, and introducing the sample directly into the container substantially prevents or reduces the decomposition of the nucleic acids that otherwise occur when the sample is stored before combining with the stabilizing agent. In addition, is has been found that the introduction of the biological sample immediately upon collection or preparation reduces or prevents gene induction.

The cationic compounds are preferred stabilizing agents since the cationic group is able to effectively attack the negatively charged groups of the nucleic acids. The cationic groups of the compound for non-covalent bonds with the negatively charged phosphate groups of the nucleic acid backbone. The hydrophilic, and particularly the aliphatic, portion of the detergent molecules form precipitatable micelles and complexes containing the nucleic acids. The resulting micelles isolate the nucleic acids from the endogenous ribonucleases to prevent enzymatic degradation. The cationic compounds produce a stabilized whole blood sample that can be transported at ambient temperature to a laboratory where the nucleic acids can be isolated from the sample.

It has been found that the recovery and stabilization of nucleic acids in the biological sample is dependent on the pH of the biological sample and stabilizing agent. The pH of the resulting mixture can range from about pH 2 to about pH 12, preferably about pH 2 to about pH 10, and more preferably about pH 3 to about pH 8. The life of the nucleic acids in this range will vary depending on the biological sample, the ratio of the amount of the biological sample to the amount of the stabilizing agent, and the particular stabilizing agent used. The shelf life of the stabilized nucleic acids in this pH can range from about 24 hours to several days.

The pH of the resulting mixture will vary depending on the biological sample being stabilized. In one embodiment of the invention, the biological sample is whole blood and the mixture of the whole blood and the stabilizing agent is adjust to about pH 2 to about pH 5. Nucleic acids stabilized with cationic compounds adjusted to about pH 2 to about pH 5 are stable at ambient temperature for several days. It has been found that optimum long term stabilization of nucleic acids in whole blood is obtained at about pH 3.6 to about pH 3.8. In other biological samples, the pH is adjusted to stabilize the mixture. For example, it has been found that eucaryotic cell cultures and bacteria are stabilized at pH 4 to about pH 8, and preferably at about pH 6 to about pH 8.

The pH of the mixture of the biological sample and stabilizing agent can be adjusted by the addition of a suitable buffer. An example of a buffer that has been found to be effective in adjusting the pH of the biological sample is tartaric acid. Other buffers and pH adjusting agents as known in the art can also be used. The pH of the buffer can be adjusted to the desired range by the addition of sodium hydroxide.

The nucleic acids, either DNA or RNA can be separated from the stabilized biological sample using various processes as known in the art. It has been found that the stabilizing agents can be separated from the nucleic acids during the purification protocol performed in the laboratory to yield the purified nucleic acid. Cationic compounds cause lysis of the cells and virus in the sample and precipitation of the nucleic acids in a complex with the compound. The precipitated nucleic acids can be extracted from the complex by a phenol extraction or by a formamide buffer as known in the art. In a further embodiment, the detergent can be solubilized to disassociate the complex and leave the insoluble nucleic acids. The compound can be solubilized by treating the complex with a concentrated solution of lithium chloride. Other methods of isolating and purifying nucleic acids are disclosed in U.S. Pat. No. 5,990,301 to Colpan et al., which is hereby incorporated by reference in its entirety.

EXAMPLE 1

Stabilization of RNA in Human Blood

This example demonstrates the effects of the ratio of the blood to stabilizing agent and the concentration of the stabilizing agent.

Twenty-four samples were prepared for this comparison. Each sample was prepared from 2.5 ml blood, drawn with a sodium citrate containing blood collection device, and mixed with 7.5 ml of a stabilization buffer containing 3% (w/v) tetradecyltrimethylammonium oxalate and 125 mM and 200 mM tartaric acid, respectively, in a 12 ml polyethylene tube. The pH of the buffer was adjusted with sodium hydroxide to 3.3, 3.5 and 3.7, respectively. Samples were stored at room temperature for 25 hours and 72 hours, respectively. In order to isolate the cellular RNA, the tubes were centrifuged at 5000×g for 10 minutes. The supernatant was discarded and the pellet was washed once with water. After additional centrifugation at 5000×g for 10 minutes, the pellet was dissolved in 300 μl of a lysis buffer, i.e., buffer RLT (QIAGEN GmbH), diluted with 360 μl water and 40 μl proteinase K were added. After a proteinase digestion for 10 minutes at 55° C. the sample was centrifuged at 20,000×g for 3 minutes, the supernatant was transferred into a new tube and 350 μl of 98% ethanol were added. The sample was then applied to a silica membrane containing spin column via centrifugation at 8000×g for 1 minute. The spin column was washed once with a GITC containing washing buffer-like buffer RW1 (QIAGEN GmbH) and two times with a ethanol containing buffer-like buffer RPE (QIAGEN GmbH). The RNA was then eluted from the silica membrane with 2×40 μl of RNase free water. All samples were processed in duplicates.

The yield of the isolated RNA was determined by measuring the optical density at 260 nm wavelength in a spectrophotometer and calculating that 1 OD260 corresponds to a concentration of 40 μg RNA/ml. The integrity of the isolated RNA was proved by electrophoresis of 30 μl of the eluate in a denaturating agarose/formaldehyde gel, stained with ethidium bromide. The yield of the RNA is presented in Table 1 and Table 2.

TABLE 1

| | 125 mM Tartaric Acid | | |
|---|---|---|---|
| Sample | pH | Storage Time (hours) | Yield (μg) |
| 1 | 3.3 | 24 | 8.4 |
| 2 | 3.3 | 24 | 7.6 |
| 3 | 3.5 | 24 | 9.5 |
| 4 | 3.5 | 24 | 9.8 |
| 5 | 3.7 | 24 | 13.3 |
| 6 | 3.7 | 24 | 17.2 |
| 7 | 3.3 | 72 | 7.2 |
| 8 | 3.3 | 72 | 6.8 |
| 9 | 3.5 | 72 | 10.3 |
| 10 | 3.5 | 72 | 10.9 |

TABLE 1-continued

125 mM Tartaric Acid

| Sample | pH | Storage Time (hours) | Yield (µg) |
|---|---|---|---|
| 11 | 3.7 | 72 | 14.8 |
| 12 | 3.7 | 72 | 16.1 |

TABLE 2

200 mM Tartaric Acid

| Sample | pH | Storage Time (hours) | Yield (µg) |
|---|---|---|---|
| 13 | 3.3 | 24 | 5.9 |
| 14 | 3.3 | 24 | 7.4 |
| 15 | 3.5 | 24 | 10.6 |
| 16 | 3.5 | 24 | 10.9 |
| 17 | 3.7 | 24 | 17.2 |
| 18 | 3.7 | 24 | 18.5 |
| 19 | 3.3 | 72 | 5.1 |
| 20 | 3.3 | 72 | 5.3 |
| 21 | 3.5 | 72 | 7.2 |
| 22 | 3.5 | 72 | 7.1 |
| 23 | 3.7 | 72 | 13.3 |
| 24 | 3.7 | 72 | 16.6 |

The results show that for the blood volume of 2.5 ml mixed with 7.5 ml of stabilization buffer containing 3% (w/v) tetradecyltrimethylammonium oxalate and 125 mM or 200 mM tartaric acid, respectively, the pH of 3.7 is optimal for the yield and integrity of the total RNA. With all pH values, the stabilization of the RNA, judged by the integrity of the ribosomal RNA, was very good, but the yield of the isolated RNA was lower with the buffers adjusted to pH 3.3 and 3.5, respectively, than with the buffer adjusted to pH 3.7. However, even the lower yields achieved with the stabilization buffer adjusted to pH 3.3 were comparable or slightly better than the yields achieved with a control method, the RNA isolation with the QIAamp® RNA Blood Mini Kit (QIAGEN Cat. No. 52303), which showed an average yield of 6.8 µg RNA per 2.5 ml of blood.

EXAMPLE 2

Northern-Blot Analysis

This example shows the results of a Northern-Blot analysis performed with blood samples from three different donors stored at room temperature for 1 hour, 24 hours, 48 hours and 72 hours. 2.5 ml blood samples, drawn with a sodium citrate containing blood collection device, were mixed with 6.9 ml of stabilization buffer containing 4% (w/v) tetradecyltrimethylammonium oxalate and 200 mM tartaric acid in a 16×100 mm polyethylene tube. Samples were stored at room temperature for 1 hour, 24 hours 48 hours and 72 hours, respectively. In order to isolate the cellular RNA, the tubes were centrifuged at 5000×g for 10 minutes. The supernatant was discarded and the pellet was washed once with water. After additional centrifugation at 5000×g for 10 minutes, the pellet was dissolved in 300 µl of a lysis buffer, i.e., buffer RLT (QIAGEN GmbH), diluted with 360 µl water and 40 µl proteinase K were added. After a proteinase digestion for 10 minutes at 55° C. the sample was centrifuged at 20,000×g for 3 minutes, the supernatant was transferred into a new tube and 350 µl of 98% ethanol were added.

The sample was then applied to a silica membrane containing spin column by centrifugation at 8000×g for 1 minute. The spin column was washed once with a GITC containing washing buffer-like buffer RW1 (QIAGEN GmbH) and two times with a ethanol containing buffer-like buffer RPE (QIAGEN GmbH). The RNA was then eluted from the silica membrane with 2×40 µl of RNase free water. A single sample was prepared for each variable. 2.5 µg of the isolated RNA were loaded onto a denaturating agarose/formaldehyde gel, and after the electrophoresis the RNA was transferred onto a nylon membrane. The nylon membrane was hybridized subsequently with a radioactive labeled RNA probe, which contained the sequence of an IFN-gamma inducible gene (GeneBank Acc.No. L07633) overnight at 60° C., washed several times at 60° C. with washing buffers containing 2×SSC/0.1% SDS to 0.5×SSC/0.1% SDS. The nylon membrane was exposed subsequently to an X-ray film. As a control, RNA from the same donor was isolated using TRIzol™ LS reagent (Life Technologies) directly after the blood draw and analyzed as described above.

The results show that the transcript levels of the IFN-gamma inducible gene, which was used as a probe to hybridize the isolated RNA, was preserved over the entire time period with no visible change in the expression level. The transcript levels were equal to the TRIzol™LS controls. These controls represent the in vivo conditions of the sample at the time point of the blood draw because the TRIzol reagent contains phenol combined with guanidine isothiocyanate and is considered as a reagent that destroys cells immediately, denatures proteins and therefore completely inhibits any biological activity. The comparison of the signal intensities from the stored samples with the TRIzol controls in the Northern-Blot analysis indicates that the transcript levels of the IFN-gamma inducible gene were "frozen" immediately after addition of the stabilization buffer to the blood sample and did not change any more during storage.

EXAMPLE 3

Comparison of Blood Collection Device with Conventional EDTA Tube

This example compares the stabilization of RNA with the collection device of the present invention and conventional EDTA containing tube.

2.5 ml blood, drawn from one donor with a blood collection device, containing 6.9 ml of stabilization buffer (4% (w/v) tetradecyltrimethylammonium oxalate, 200 mM tartaric acid, pH 3.7) in a 16×100 mm polyethylene tube closed with a HEMOGARD™ closure (Becton, Dickinson and Company) and evacuated to a defined vacuum that drawed 2.5 ml of blood when connected to the vein of the donor. Samples were stored at room temperature for 1 hour, 1 day, 3 days, 7 days and 10 days, respectively. In order to isolate the cellular RNA, the tubes were centrifuged at 5000×g for 10 min. The supernatant was discarded and the pellet was washed once with water. After additional centrifugation at 5000×g for 10 min, the pellet was dissolved in 360 µl of a resuspension buffer containing ammonium acetate and then 300 µl of a lysis buffer, i.e., buffer RLT (QIAGEN GmbH), and 40 µl proteinase K were added. After a proteinase digestion for 10 minutes at 55° C., the sample was centrifuged at 20,000×g for 3 minutes, the supernatant was transferred into a new tube and 350 µl of 98% ethanol were added. The sample was then applied to a silica membrane containing spin column by centrifugation at 8000×g for 1 minute. The spin column was washed once with a GITC containing washing buffer-like buffer RW1 (QIAGEN GmbH) and two times with a ethanol containing buffer-like buffer RPE (QIAGEN GmbH).

A digestion of the residual genomic DNA which could be co-purified with the RNA in low amounts was performed on the silica membrane according to the instructions in the manual of the RNase-Free DNase Set (QIAGEN GmbH Cat.No. 79254). The RNA was eluted from the silica membrane with 2×40 μl of elution buffer. All samples were processed in duplicates. For the analysis, the eluates were diluted 1:125 fold and 1 μl of the diluted eluate was analyzed by real time TaqMan RT-PCR. The mRNA of the GAPDH-gene was amplified using an assay developed by Perkin Elmer. Each sample was analyzed in duplicate in the TaqMan RT-PCR amplification.

As a control, RNA from the same donor was drawn with a Becton Dickinson Vacutainer EDTA tube and was stored in this tube for the same time period as described above. The RNA from 1 ml of the stored blood sample was isolated at each time point using TRIzol™ LS reagent (Life Technologies). The isolated RNA was subsequently cleaned up according to the RNeasy™ Mini protocol for the RNA clean up (QIAGEN Cat.No. 74103). The RNA was eluted with 2×40 μl of RNase-free water. The eluate was diluted 1:50 fold in order to compensate for the lower sample volume processed with the TRIzol method, compared to the 2.5 ml of blood in the sample tubes. The samples were analyzed using also the GAPDH TaqMan RT-PCR system from Perkin Elmer.

The real time RT-PCR results show that in the unpreserved EDTA blood, the transcript level decreases over time (indicated by the increasing ct value in the TaqMan analysis) up to a degree of degradation after 7 to 10 days at which point the mRNA is no longer detectable. On the other hand, the GAPDH mRNA in the preserved samples does not show any decrease in copy number, taking into consideration that the error range of the TaqMan assay is ±1 ct value. Within this error range, all changes in the ct value have to be considered as normal fluctuations of the amplification system and no degradation is visible. This result clearly indicates the advantage of the new developed blood collection device over the EDTA blood collection tube and also makes clear that the stabilization of the RNA is a prerequisite for the molecular analysis of the sample material. It was also possible to isolate the genomic DNA from the stabilized blood sample. Table 3 shows the results for the stabilization of genomic DNA in human blood. After 24 hour and 72 hours of storage at room temperature, isolated genomic DNA was of high molecular weight. The main band migrated at a length greater than 20 kb. The yield was in the range between 47 to 80 μg per 2.5 ml of blood, which is within the expected yield range for this amount of blood. The DNA was also applicable to enzymatic reactions like restriction endonuclease digestion and PCR amplification.

TABLE 3

| storage at room temp. | NA stabilization device/ct value | mean value/ct | EDTA tube/ct value | mean value/ct |
|---|---|---|---|---|
| 1 h | 33.38 | | 30.17 | |
| | 31.42 | | 29.63 | |
| | | 31.48 | | 30.58 |
| | 31.06 | | 32.29 | |
| | 30.06 | | 30.24 | |
| 1 day | 31.28 | | 30.18 | |
| | 28.62 | | 29.35 | |
| | | 30.11 | | 31.26 |
| | 30.34 | | 33.2 | |
| | 30.19 | | 32.32 | |
| 3 days | 31.27 | | 33.33 | |
| | 31.92 | | 32.37 | |
| | | 30.91 | | 36.32 |
| | 30.15 | | 40 | |
| | 30.3 | | 39.58 | |

TABLE 3-continued

| storage at room temp. | NA stabilization device/ct value | mean value/ct | EDTA tube/ct value | mean value/ct |
|---|---|---|---|---|
| 7 days | 33.03 | | 40 | |
| | 31.16 | | 39.01 | |
| | | 32.58 | | 38.4 |
| | 34.21 | | 37.67 | |
| | 31.9 | | 36.12 | |
| 10 days | 34.2 | | 40 | |
| | 32.47 | | 40 | |
| | | 32.58 | | 38.97 |
| | 32.36 | | 38.38 | |
| | 31.29 | | 37.48 | |

EXAMPLE 4

Stabilization of Genomic DNA in Whole Blood 2.5 ml blood, drawn with a sodium citrate containing blood collection device, were mixed with 6.9 ml of stabilization buffer containing 4% (w/v) tetradecyltrimethylammonium oxalate and 200 mM tartaric acid in a 16×100 mm polyethylene tube. Samples were stored at room temperature for 24 hours and 72 hours, respectively. In order to isolate the genomic DNA, the tubes were centrifuged at 5000×g for 10 min. The supernatant was discarded and the pellet was washed once with water. After additional centrifugation at 5000×g for 10 minutes, the pellet was dissolved in 300 μl of a EDTA and sodium chloride containing buffer and 400 μl of a lysis buffer, i.e., buffer AL (QIAGEN GmbH), and 20 μl proteinase K were added. After a proteinase digestion for 10 minutes at 65° C., 420 μl of 98% ethanol were added. The sample was then applied to a silica membrane containing spin column by centrifugation at 8000×g for 1 minute. The spin column was washed once with a guanidine hydrochloride containing washing buffer-like buffer AW1 (QIAGEN GmbH) and once with an ethanol containing buffer-like buffer AW2 (QIAGEN GmbH). The DNA was then eluted from the silica membrane with 300 μl of a tris-buffer.

5 μl of the eluate was analyzed on a 0.8% agarose/TBE gel stained with ethidium bromide. The yield of the isolated DNA was determined by measuring the optical density at 260 nm wavelength in a spectrophotometer and calculating that 1 OD260 corresponds to a concentration of 50 μg DNA/ml.

The genomic DNA was also applied to enzymatic reactions like restriction enzyme digestion or PCR amplification. For the restriction endonuclease digestion, 2 μg of the DNA was digested with 6 U EcoRI (E) and Hind III (H), respectively, for 3 hours at 37° C. and analyzed subsequently on a 0.8 % agarose TBE gel. For the PCR amplification, 150 and 300 ng of the DNA were added to a 50 μl total volume PCR reaction mix and a 1.1 kb fragment of the human homologue of giant larvae-gene was amplified. The PCR products were analyzed on a 1.2% agarose/TBE gel.

While various embodiments have been chosen to demonstrate the invention, it will be understood by those skilled in the art that various modifications and additions can be made without departing from the scope of the invention as defined in the appended claims.

What is claimed is:

1. An apparatus for collecting a biological sample, said apparatus comprising:
   a container defining an internal chamber, and a closure closing an open end, said internal chamber having a pressure less than atmospheric pressure for drawing a predetermined volume of said biological sample in said container, and at least one nucleic acid stabilizing agent contained within said container in an amount effective to stabilize and prevent nucleic acid degradation in said biological sample where said at least one stabilizing agent comprises a cationic detergent.

2. The apparatus of claim 1, wherein said biological sample is whole blood.

3. The apparatus of claim 1, wherein said at least one stabilizing agent is an aqueous solution and said at least one stabilizing agent further comprises a component selected from the group consisting of chaotropic salts, ribonuclease inhibitors, chelating agents, and mixtures thereof, and wherein said aqueous solution of said stabilizing agent has a pH of about pH 2 to about pH 12.

4. The apparatus of claim 3, wherein said aqueous solution has a pH of about pH 2 to about pH 10.

5. The apparatus of claim 3, wherein said aqueous solution has a pH of about pH 3 to about pH 8.

6. The apparatus of claim 3, wherein said at least one stabilizing agent is included in an amount to lyse cells in said biological sample.

7. The apparatus of claim 6, wherein said at least one stabilizing agent lyses reticulocytes, bacteria, red blood cells, white blood cells, and viruses.

8. The apparatus of claim 3, wherein said at least one stabilizing agent is included in an amount effective to prevent gene induction in said biological sample.

9. The apparatus of claim 3, wherein said chaotropic salt is selected from the group consisting of guanidinium isocyanate and guanidinium hydrochloride.

10. The apparatus of claim 3, wherein said ribonuclease inhibitor is placental RNAse inhibitor protein.

11. The apparatus of claim 1, wherein said at least one stabilizing agent has the general formula $$YR_1R_2R_3R_4X$$

wherein Y is nitrogen or phosphorous;
$R_1$, $R_2$, $R_3$, and $R_4$ are independently selected from the group consisting of branched alkyl, non-branched alkyl, $C_6$–$C_{20}$ aryl, and $C_6$–$C_{26}$ aralkyl; and
X is an anion.

12. The apparatus of claim 11, wherein X is an anion selected from the group consisting of phosphate, sulfate, formate, acetate, propionate, oxalate, malonate, succinate, citrate, bromide and chloride.

13. The apparatus of claim 11, wherein Y is nitrogen and said at least one stabilizing agent is a quaternary amine.

14. The apparatus of claim 11, wherein said $R_1$ is an alkyl having 12, 14, or 16 carbon atoms and $R_2$, $R_3$, and $R_4$ are methyl.

15. The apparatus of claim 11, wherein said at least one stabilizing agent further comprises at least one proton donor in an effective amount to stabilize nucleic acids in said sample.

16. The apparatus of claim 15, wherein said proton donor is selected from the group consisting of alkenyl carboxylic acids, $C_2$–$C_6$ aliphatic mono- and dicarboxylic acids, aliphatic ketodicarboxylic acids, amino acids, mineral acids and mixtures thereof.

17. The apparatus of claim 15, wherein said at least one proton donor is a carboxylic acid.

18. The apparatus of claim 17, wherein said at least one proton donor is selected from the group consisting of acetic acid, propionic acid, n-butanoic acid, n-pentanoic acid, isopentanoic acid, 2-methylbutanoic acid, 2,2 dimethylpropionic acid, n-hexanoic acid, n-octanoic acid, n-decanoic acid, dodecanoic acid, methacrylic acid, butenoic acid, isobutenoic acid, tartaric acid and malic acid.

19. The apparatus of claim 17, wherein said at least one proton donor is tartaric acid.

20. The apparatus of claim 1, wherein said at least one stabilizing agent is tetradecyltrimethyl ammonium oxalate.

21. A method of stabilizing nucleic acids in a biological sample comprising the steps of:

providing a sample collection container having a side wall, and a bottom defining an internal chamber, said container containing at least one nucleic acid stabilizing agent in an amount sufficient to stabilize and prevent nucleic acid degradation of said biological sample and where said at least one stabilizing agent comprises a cationic detergent; and collecting a biological sample directly from a patient into said container and immediately mixing said biological sample with said at least one stabilizing agent to form a stabilized biological sample and substantially prevent nucleic acid degradation.

22. The method of claim 21, wherein said at least one stabilizing agent is an aqueous medium and where said at least one stabilizing agent further comprises a component selected from the group consisting of chaotropic salts, ribonuclease inhibitors, chelating agents, and mixtures thereof.

23. The method of claim 22, wherein said at least one stabilizing agent is a cationic compound having the general formula $$YR_1R_2R_3R_4X$$

wherein Y is nitrogen or phosphorous;
$R_1$, $R_2$, $R_3$, and $R_4$ are independently selected from the group consisting of branched alkyl, non-branched alkyl, $C_6$–$C_{20}$ aryl, and $C_6$–$C_{26}$ aralkyl; and
X is an anion.

24. The method of claim 23, wherein X is selected from the group consisting of phosphate, sulfate, formate, acetate, propionate, oxalate, malonate, succinate, citrate, bromide and chloride.

25. The method of claim 23, wherein said $R_1$ is an alkyl having 12, 14, or 16 carbon atoms and $R_2$, $R_3$, and $R_4$ are methyl.

26. The method of claim 23, wherein Y is nitrogen.

27. The method of claim 23, wherein said at least one stabilizing agent further comprises at least one proton donor in an effective amount to stabilize nucleic acids in said sample.

28. The method of claim 23, wherein said at least one proton donor is selected from the group consisting of alkenyl carboxylic acids, $C_2$–$C_6$ aliphatic mono- and dicarboxylic acids, aliphatic ketodicarboxylic acids, amino acids, mineral acids and mixtures thereof.

29. The method of claim 22, wherein said aqueous medium has a pH of about pH 3 to about pH 8.

30. The method of claim 22, wherein said chaotropic salt is selected from the group consisting of guanidinium isothiocyanate and guanidinium hydrochloride.

31. The method of claim 22, wherein said ribonuclease inhibitor is placental RNAse inhibitor protein.

32. The method of claim 21, wherein said container has an internal pressure less than atmospheric pressure, said method comprising drawing a predetermined volume of said biological sample directly into said container and mixing with a stabilizing amount of said at least one stabilizing agent.

33. The method of claim 32, wherein said biological sample is whole blood and said method comprises withdrawing said whole blood sample from a patient and introducing said whole blood sample directly into contact with said at least one stabilizing agent in said sample collection container to lyse cells and stabilize nucleic acids in said whole blood sample.

34. The method of claim 21, wherein said biological sample is selected from the group consisting of red blood cell concentrates, platelet concentrates, leukocyte concentrates, plasma, serum, urine, bone marrow aspirates, tissue, and cerebral spinal fluid.

35. The method of claim 21, wherein said at least one stabilizing agent is included in an amount to inhibit gene induction in said biological sample.

36. A method of collecting and stabilizing a whole blood sample, said method comprising:

providing a sample collection container having a side wall, a bottom wall and a closure member forming an internal chamber, said container enclosing an effective amount of an aqueous solution or dispersion of a proton donor and a nucleic acid stabilizing agent to stabilize and preserve nucleic acids in a whole blood sample, said internal chamber having pressure less than atmospheric pressure; and collecting a whole blood sample directly from a patient into said collection container and mixing said blood sample with said stabilizing agent to form a stable whole blood sample.

37. The method of claim 36, wherein said closure member is a septum and said method comprises piercing said septum with a cannula and introducing said whole blood sample through said cannula into said collection container.

38. The method of claim 36, wherein said stabilizing agent is selected from the group consisting of cationic compounds, detergents, chaotropic salts, ribonuclease inhibitors, chelating agents, and mixtures thereof, and wherein said aqueous solution or dispersion has a pH of about pH 2 to about pH 12.

39. The method of claim 38, wherein said stabilizing agent has the general formula $$YR_1R_2R_3R_4X$$

wherein Y is nitrogen or phosphorous $R_1$, $R_2$, $R_3$, and $R_4$ are independently selected from the group consisting of branched alkyl, non-branched alkyl, $C_6$–$C_{20}$ aryl, and $C_6$–$C_{26}$ aralkyl; and X is an anion.

40. The method of claim 36, wherein said aqueous solution or dispersion has a pH of about pH 2 to about pH 5.

41. The method of claim 36, wherein said aqueous solution or dispersion has a pH of about 3.6 to about pH 3.8.

42. The method of claim 36, wherein said stabilizing agent is selected from the group consisting of guanidinium isothiocyanate, guanidinium hydrochloride, sodium dodecylsulfate, polyoxyethylene sorbitan monolaurate, placental RNAse inhibitor protein, and mixtures thereof.

43. The method of claim 36, wherein said proton donor is selected from the group consisting of alkenyl carboxylic acids, $C_2$–$C_6$ aliphatic mono- and dicarboxylic acids, aliphatic ketodicarboxylic acids, amino acids, mineral acids and mixtures thereof.

44. An apparatus for collecting a biological sample, said apparatus comprising:

a container defining an internal chamber, and a closure closing an open end, and a proton donor and at least one stabilizing agent contained within said container in an amount effective to stabilize and preserve said biological sample.

45. The apparatus of claim 44, wherein said at least one stabilizing agent is an aqueous solution of a stabilizing agent selected from the group consisting of cationic compounds, detergents, chaotropic salts, ribonuclease inhibitors, chelating agents, and mixtures thereof, and wherein said aqueous solution of said stabilizing agent has a pH of about pH 2 to about pH 12.

46. The apparatus of claim 44, wherein said at least one stabilizing agent has the general formula $$YR_1R_2R_3R_4X$$

wherein Y is nitrogen or phosphorous;

$R_1$, $R_2$, $R_3$, and $R_4$ are independently selected from the group consisting of branched alkyl, non-branched alkyl, $C_6$–$C_{20}$ aryl, and $C_6$–$C_{26}$ aralkyl; and X is an anion.

47. A method of stabilizing a biological sample comprising the steps of:

providing a sample collection container having an internal chamber, said container containing a proton donor and at least one stabilizing agent in an amount sufficient to stabilize and preserve a biological sample; and obtaining a biological sample and immediately thereafter introducing said biological sample into said container and mixing said biological sample with said at least one stabilizing agent to form a stabilized biological sample.

48. The method of claim 47, wherein said at least one stabilizing agent is in an aqueous medium containing a component selected from the group consisting of cationic compounds, detergents, chaotropic salts, ribonuclease inhibitors, chelating agents, and mixtures thereof.

49. The method of claim 47, wherein said at least one stabilizing agent is a cationic compound having the general formula $$YR_1R_2R_3R_4X$$

wherein Y is nitrogen or phosphorous;

$R_1$, $R_2$, $R_3$, and $R_4$ are independently selected from the group consisting of branched alkyl, non-branched alkyl, $C_6$–$C_{20}$ aryl, and $C_6$–$C_{26}$ aralkyl; and X is an anion.

50. The method of claim 49, wherein X is selected from the group consisting of phosphate, sulfate, formate, acetate, propionate, oxalate, malonate, succinate, citrate, bromide and chloride.

51. The method of claim 47, wherein said proton donor is selected from the group consisting of acetic acid, propionic acid, n-butanoic acid, n-pentanoic acid, isopentanoic acid, 2-methylbutanoic acid, 2,2 dimethylpropionic acid, n-hexanoic acid, n-octanoic acid, n-decanoic acid, dodecanoic acid, methacrylic acid, butenoic acid, isobutenoic acid, tartaric acid, and malic acid.

* * * * *